(12) United States Patent
Dockhorn

(10) Patent No.: US 12,569,333 B2
(45) Date of Patent: Mar. 10, 2026

(54) PACKAGING FOR SHIPPING AND STORING INTRAOCULAR LENSES

(71) Applicant: MEDICEL AG, Altenrhein (CH)

(72) Inventor: Volker Dockhorn, Altenrhein (CH)

(73) Assignee: MEDICEL AG, Altenrhein (CH)

( * ) Notice: Subject to any disclaimer, the term of this patent is extended or adjusted under 35 U.S.C. 154(b) by 691 days.

(21) Appl. No.: 17/765,433

(22) PCT Filed: Sep. 30, 2020

(86) PCT No.: PCT/CH2020/050010
§ 371 (c)(1),
(2) Date: Mar. 30, 2022

(87) PCT Pub. No.: WO2021/062568
PCT Pub. Date: Apr. 8, 2021

(65) Prior Publication Data
US 2022/0354635 A1     Nov. 10, 2022

(30) Foreign Application Priority Data

Sep. 30, 2019     (CH) ...................................... 01235/19

(51) Int. Cl.
*A61F 2/16*         (2006.01)
*A61B 50/00*        (2016.01)
(Continued)

(52) U.S. Cl.
CPC ............. *A61F 2/1691* (2013.01); *B65B 55/18* (2013.01); *A61B 2050/0065* (2016.02);
(Continued)

(58) Field of Classification Search
CPC ....... A61F 2/1691; B65B 55/10; B65B 55/18; A61B 50/33; A61B 2050/0065; A61B 2050/3008
(Continued)

(56) References Cited

U.S. PATENT DOCUMENTS 4,173,281 A * 11/1979 Trought ................ A61F 2/1691
                                                          206/439
4,269,307 A * 5/1981 LaHaye ................ A61F 2/1691
                                                          220/345.4
(Continued)

FOREIGN PATENT DOCUMENTS

EP          0401163 A1     12/1990
EP          0726694 A2     8/1996
(Continued)

OTHER PUBLICATIONS

International Search Report for International Application No. PCT/CH2020/050010; mailed Dec. 14, 2020.
(Continued)

*Primary Examiner* — Joshua G Kotis
(74) *Attorney, Agent, or Firm* — MORRISS O'BRYANT COMPAGNI CANNON, PLLC

(57)     ABSTRACT

A method for manufacturing a packaging with an intraocular lens enclosed therein includes insertion of the intraocular lens into a packaging comprising a first packaging material which is gas-tight in a first sub-section, and a second packaging material which is permeable to gases in a second sub-section, first sealing of the packaging so that the intraocular lens is enclosed in the interior space of the packaging, the interior space being partially delimited by the first sub-section and the second sub-section, sterilization of the interior space of the packaging by exposing the packaging to a gas, so that the gas can penetrate through the second sub-section into the interior space of the packaging, (Continued)

second sealing of the packaging by sealing off a volume of the gas-tight first sub-section of the packaging with the intraocular lens enclosed therein from the volume of the second sub-section.

19 Claims, 4 Drawing Sheets

(51) Int. Cl.
    *B65B 25/00*         (2006.01)
    *B65B 55/18*         (2006.01)
    *A61B 50/33*         (2016.01)
    *B65B 55/10*         (2006.01)
(52) U.S. Cl.
    CPC ............. *A61B 50/33* (2016.02); *B65B 25/008*
                      (2013.01); *B65B 55/10* (2013.01)
(58) Field of Classification Search
    USPC ......................................... 53/425, 432, 407
    See application file for complete search history.

(56)                      References Cited

U.S. PATENT DOCUMENTS

| | | | | |
|---|---|---|---|---|
| 4,402,396 | A | * | 9/1983 | Graham ................ A61F 2/1691 |
| | | | | 356/246 |
| 4,482,053 | A | * | 11/1984 | Alpern ...................... A61L 2/26 |
| | | | | 206/439 |
| 5,348,752 | A | * | 9/1994 | Gorlich ................... B65B 7/168 |
| | | | | 229/123.1 |
| 5,439,132 | A | * | 8/1995 | Gorlich ............. B65D 81/2076 |
| | | | | 220/276 |

| | | | | |
|---|---|---|---|---|
| 6,622,864 | B1 | * | 9/2003 | Debbs .................... A61B 50/30 |
| | | | | 206/363 |
| 10,293,965 | B2 | * | 5/2019 | Lu .............................. B65B 7/02 |
| 2004/0081601 | A1 | * | 4/2004 | Morrissey ................. A61L 2/26 |
| | | | | 422/26 |
| 2007/0084144 | A1 | | 4/2007 | Labrecque et al. |
| 2007/0250068 | A1 | * | 10/2007 | Vincent-Aubry ..... A61F 2/1678 |
| | | | | 606/107 |
| 2012/0124943 | A1 | * | 5/2012 | Nakamura .............. B65B 55/18 |
| | | | | 53/425 |
| 2012/0205269 | A1 | * | 8/2012 | Ludvig ..................... A61L 2/00 |
| | | | | 206/363 |
| 2015/0114855 | A1 | * | 4/2015 | Glick ..................... B65D 81/18 |
| | | | | 206/5 |
| 2015/0223931 | A1 | * | 8/2015 | Glick ................... A61F 2/1691 |
| | | | | 206/229 |
| 2016/0135895 | A1 | * | 5/2016 | Faasse .................... B65B 55/02 |
| | | | | 53/425 |
| 2020/0361684 | A1 | * | 11/2020 | Clarke ................... B65B 51/10 |
| 2023/0181010 | A1 | * | 6/2023 | Suzuki .............. A61B 1/00147 |
| | | | | 53/443 |

FOREIGN PATENT DOCUMENTS

| | | | | | |
|---|---|---|---|---|---|
| FR | | 2820118 | A1 | 8/2002 | |
| WO | WO-2006102450 | A2 | * | 9/2006 | ............. G02C 13/00 |
| WO | | 2015061401 | A1 | 4/2015 | |
| WO | | 2015183432 | A1 | 12/2015 | |

OTHER PUBLICATIONS

Written Opinion of the International Searching Authority for International Application No. PCT/CH2020/050010; mailed Dec. 14, 2020.

* cited by examiner

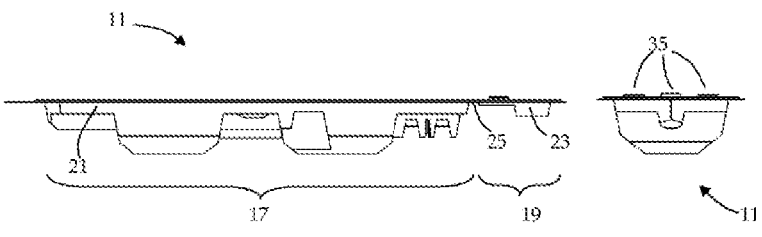
Fig. 3                              Fig. 4
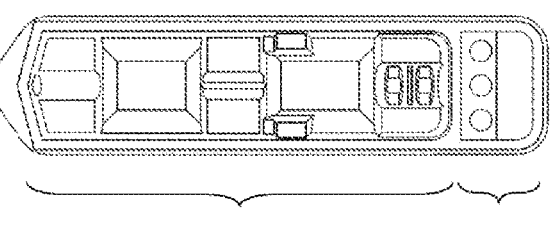
Fig. 5
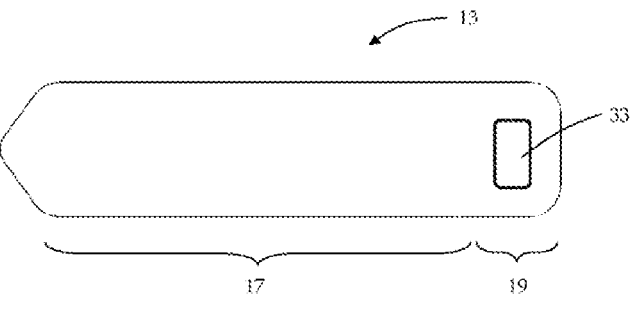
Fig. 6

PACKAGING FOR SHIPPING AND STORING INTRAOCULAR LENSES

CROSS-REFERENCE TO RELATED APPLICATIONS

This application is a national phase entry under 37 U.S.C § 371 of PCT/CH2020/050010 filed Sep. 30, 2020, which claims priority to Swiss Patent Application No. 01235/19 filed Sep. 30, 2019, the entirety of each of which is incorporated by this reference.

TECHNICAL FIELD OF THE INVENTION

The invention relates to a method for manufacturing a packaging with a sterile and substantially gas-tight intraocular lens enclosed therein, in particular an intraocular lens preloaded in an injector. Furthermore, the invention relates to a lens pack, in particular an injector pack, which contains a sterile intraocular lens and can be produced by the method mentioned. The invention also relates to a lens pack or injector pack semi-finished product.

BACKGROUND OF THE INVENTION

Hydrophilic intraocular lenses and some hydrophobic intraocular lenses are traditionally stored wet to maintain adequate hydration and thus flexibility of the lenses until they are injected into an eye. The flexibility is necessary so that the lenses can be folded for injection into an eye.

In general, medical or surgical instruments are usually prepared for storage by sterilizing them while packaged in a sterilizable material by introducing sterilizing gases, such as EtO or steam, at controlled temperature and, if necessary, controlled pressure. In the case of steam sterilization, this is carried out in an autoclave. Common parameters for steam sterilization are, for example, 121° C./20 min or 134° C./min, whereby care must be taken to ensure good steam permeability of the packaging. The gas or steam introduced during sterilization escapes from the packaging after the sterilization process. Such generally known gas sterilization processes are thus not suitable for packaging and storage of intraocular lenses to be stored wet, since the packaging materials that allow penetration of the gases or steam do not also represent a permanent barrier to humidity and thus wet storage cannot be guaranteed.

Materials to be stored wet are therefore usually sterilized in liquid-filled packaging that can be sealed in a water and air-tight manner. These materials can still be sterilized by steam in an autoclave, however, in such a case the sterilization process is different. Since the steam itself cannot penetrate the packaging, sterilization here takes place by means of a heat exchange via the packaging materials to the liquid contained in the packaging. Over the course of validations, it must be determined after what time period the liquid reaches a sufficiently high temperature for sterilization, and only then does the actual sterilization begin. As a rule, in this type of sterilization, a limited overpressure is applied, which is at least such that the liquid inside the packaging does not begin to boil even when the sterilization temperature is reached. As a rule, an attempt is made to fill the packaging with as much liquid as possible and only a minimum amount of residual air, since the residual amount of air expands greatly at elevated temperatures and exerts a very high internal pressure on the packaging, which can, in particular, lead to the sealing seams bursting in packagings with sealed covers. In general, the higher the quantity of air, the higher the pressure created inside the packaging. However, since the ruggedness of the sealing seam cannot be increased arbitrarily, inasmuch as this seam also serves the end user for opening of the packaging, and insofar as the back pressure of the autoclave can also not be increased arbitrarily, as this leads to deformations of the packaging and possibly of the product itself, it is required, when using this method of autoclaving by means of heat exchange, to use plenty of water and very little air in the packaging. A method for packaging foldable hydrophilic intraocular lenses is described in disclosure WO2015061401. The method comprises storing the foldable lens in a substantially airtight container that contains a water reservoir that is not in direct contact with the lens. The lens may thereby be stored in unfolded state in an injector which is stored together with the lens in the airtight container, wherein the container is provided with a water reservoir, which water reservoir is not in direct contact with the lens.

Disclosure WO2015183432 describes a similar method for maintaining a hydrophilic intraocular lens in a foldable state without the lens being immersed in fluid. The method includes storing the foldable lens in a substantially airtight container containing free water. The lens is thereby disposed within the container in a location where the lens is not immersed in liquid. A combination is furthermore disclosed, comprising, on the one hand, an airtight container containing free water, and, on the other hand, a foldable hydrophilic lens stored within the container in a location where the lens is not immersed in water. The packaging method by which this condition is achieved typically comprises the following steps: a) insertion of the injector loaded with the intraocular lens into a holder, b) placement of the holder into the container, c) before closing the container, delivery of a desired volume of free water (by adding droplets or by spraying) to the inside of the container, d) sealing of the container.

The volume of water contained in the pouch after sealing is between about 5 ml and about 20 ml according to WO2015061401 or between about 0.5 ml and about 3 ml according to WO2015183432. It is furthermore stated in the documents that the airtight container with the lens can be autoclaved, which is to say, that it can withstand being heated to 121° C. or more for a time period of half an hour or more.

On the basis of this information relating to the possible autoclaving, the question arises whether it is possible to achieve sterilization, which is normally required for medical or surgical instruments and implants. In particular, according to indications of disclosures WO2015061401 and WO2015183432, apparently airtight packaging, containing a very minimal volume of water when compared to the packaging volume, is heated. As previously described, such a method requires that the heating of the water contained in the gas-tight packaging must take place via a heat exchange from the packaging material to the interior of the packaging. As a result of the fact that much more air is present in the container relative to the amount of water, heating the air and liquid to sterilization temperature is a relatively lengthy process. In addition, the internal pressure due to the expansion of the heated air is very high, so that either an autoclave must be operated with extremely high counter-pressure, or the packaging must be very sturdily designed. This sturdy design, on the other hand, makes opening the packaging, which is usually done by pulling the cover film open, almost impossible and very uncomfortable for the user. Furthermore, it is necessary to determine the point in time in which the water contained in the hermetically sealed packaging turns into steam and the desired sterilization temperature is achieved. For these reasons, the application of this method can be cumbersome or complex and thereby ultimately expensive for the manufacturer. In particular, it is difficult to guarantee the achievement of an effective sterilization and thereby sterility of the packaged intraocular lens. Moreover, uncertainty remains as to whether sterilization has actually taken place or whether it has taken place to a sufficient extent. In medical applications, in particular the packaging of implants, such risks are intolerable. Packaging and sterilization processes according to WO2015061401 and WO2015183432, which involve heating a large, gas-tight volume of air with only a small amount of water, are therefore considered unsuitable for use with intraocular lenses. There is therefore a need to provide a sterilization process that is as safe and cost-effective as possible in order to improve product quality and product safety.

A sterilization and packaging envelope is moreover disclosed in the disclosure document FR 2820118 A1. This includes, on the one hand, a first chamber for sterilizing medical instruments by means of gas treatment (sterilization chamber) and, on the other hand, a second chamber for storing the sterilized medical instruments (storage chamber). The first chamber has a porous wall portion that allows the contents enclosed therein to be sterilized by treating them with a gas. This first chamber is separated from the sterile second chamber by means of a removable seal, so that after sterilization, the items can be transferred from the first to the second chamber for storage. For this to work, both chambers are initially separated by a seal. The completely sealed packaging is initially gamma-sterilized so that both chambers are sterile, thereinafter the first chamber with the porous wall section is opened and the item(s) to be sterilized is/are introduced into the first chamber. The opening in the first chamber is then sealed. Autoclaving is then performed to sterilize the first chamber and thus the item(s) in the first chamber. Subsequent to the autoclaving, the sealing between the two chambers is opened and the item(s) that had previously been sterilization-treated is/are transferred from the first chamber to the second chamber. Thereinafter, a new seal is created between the two chambers. In so doing, the sterilized item is now enclosed in the second chamber. This is a relatively complex process, since, on the one hand, it involves at least two sealing steps and one unsealing step, as well as, on the other hand, two sterilization steps using different sterilization methods, this in order to ultimately package an object in an airtight and sterile manner.

A method for sterilizing and packaging a chemically sensitive medical product or device, such as, for example, an implant, is provided in the disclosure document US2007/0084144 A1. In this method, the medical product or device has a coating derived from a vitamin E compound, fish oil, or a combination thereof. The steps of the method include: provision of the medical product or device; provision of a pouch having a non-permeable chamber and a gas permeable head portion; placement of the medical product or device in the pouch; sealing of the pouch along the gas permeable head portion such that the non-permeable chamber remains accessible through the gas permeable head portion; sterilization of the medical product or device with a sterilizing agent that is guided through the gas permeable head portion into the non-permeable chamber, wherein the sterilization is performed at a temperature between about 20° C. and 40° C.; sealing of the medical product or device in the chamber within the impermeable pouch; and optionally, removal of the head portion, wherein the medical product or device remains packaged and sterilized in the non-permeable chamber. According to the disclosure, the sterilizing agent can be, for example, ethylene oxide (EtO) gas, steam, gas plasma, vaporized hydrogen peroxide, gamma radiation, or electron beam radiation.

In the disclosure document US2007/0084144 A1, the solution involves a simple pouch. The disadvantage to this method is that an article packed in a pouch is insufficiently protected against external mechanical influences, since a pouch can, for example, be pressed in during storage and transport.

Task

One of the tasks of the present invention is therefore to provide an alternative method for the introduction of humidity into packaging and for sterilization of the packaging of ready-to-use intraocular lenses, in particular of sets with injector and intraocular lens. The method shall, in particular, be such that a certain amount of humidity is still present in the packaging after sterilization, whereby wet storage of intraocular lenses under sterile conditions can be enabled. In addition, the process should be simple and inexpensive and applicable under variable packaging conditions, and/or with variable or different packaging volumes. In this manner, a packaged product, in particular a packaged ready-to-use intraocular lens or a packaged ready-to-use set with injector and intraocular lens, which is packaged and sterilized by means of the alternative method, is to be provided. A task of the present invention is, in particular, to provide a packaged product in which an intraocular lens is stored wet under sterile conditions. Another task is to provide a packaging in which the intraocular lens is protected from mechanical influences. Another task is to provide a space-saving packaging in which the intraocular lens is protected from mechanical influences.

SUMMARY OF THE INVENTION

The above-mentioned task is solved by means of a lens pack product or injector pack product, a packaging and the method of the present invention. The invention further relates to semi-finished and/or finished packaging products. In this, finished means, in particular, that the product is sterilely packaged in a packaging with controlled atmosphere.

The invention relates, in particular, to a method for manufacturing a packaging with an intraocular lens enclosed therein in a sterile and substantially gas-tight manner, in particular, for example, a loading chamber with a preloaded lens or an injector with a preloaded lens, hereinafter also referred to as a lens pack (lens packaging) or injector pack (injector packaging), comprising the following steps:

insertion of an intraocular lens (optionally with holder, loading chamber and/or injector) into an interior space of a packaging, wherein the packaging, in a first sub-section, consists of a first packaging material which is substantially gas-tight, and in a second sub-section, comprises a second packaging material which is permeable to gases or gas mixtures, such as, for example, at least steam and optionally other gaseous sterilizing substances, first sealing of the packaging so that the intraocular lens is enclosed in the interior space of the packaging, which interior space is partly delimited by the first sub-section and partly by the second sub-section (which is to say, both sub-sections of the packaging together define the aforementioned interior space, which forms a coherent volume), sterilization of the interior space of the packaging sealed according to the first sealing, by exposing the packaging sealed according to the first sealing, after the first sealing, for sterilization to a gas or gas mixture, such as, for example, steam (and other optional gaseous sterilizing substances) or other gaseous sterilizing substances, so that the gas or gas mixture, such as, for example, the steam (and the other optional gaseous sterilizing substances) or the other gaseous sterilizing substances, can penetrate through the second sub-section into the interior space of the packaging, second sealing of the packaging, by sealing off at least one portion of the volume of the gas-tight first sub-section of the packaging, with the intraocular lens enclosed therein, from the volume of the second sub-section, whereby the intraocular lens is completely packaged within the gas-tight first packaging material (or in other words, a second sealing of the packaging, by sealing off at least a first portion of the volume of the interior space, which is located in the gas-tight first sub-section of the packaging, with the intraocular lens contained therein, from a second volume portion which is located in the second sub-section of the packaging, whereby the intraocular lens is completely packaged in the gas-tight first packaging material.

In an optional further step, after the second sealing, the second part of the packaging, which is important for creating the gas atmosphere but is no longer useful in a finished product, can be detached.

This method allows for improved humidity control by adjusting or being able to adjust the humidity of the atmosphere in the packaging after the first sealing, for example, during the sterilization step of the atmosphere used for sterilization by virtue of a gas permeable sub-section of the packaging.

Air saturated with steam at elevated temperature is preferably used for sterilization, which air can enter the packaging via the gas permeable sub-section. Optionally, further sterilizing substances can be added to the air. Water is thus added directly in its gaseous aggregate state, which is to say, as steam. The addition of water in its liquid state can be dispensed with or is only used as a reserve to compensate for a loss of water over the lifespan of the product. An excessive content of liquid water in the final product or finished product intended for sale can thus be avoided.

Sterilization is expediently carried out in an autoclave. An autoclave is preferably a container that can be sealed in a gas-tight manner, preferably a pressure container, which is used for the thermal treatment of material to be treated, preferably in the overpressure range. In the autoclave, gas composition, temperature and pressure can preferably be adjusted and/or controlled for the purpose of sterilization treatment.

A definitive gas-tight sealing (which is to say, the second sealing) of the packaging of the lens is only undertaken after carrying out the sterilization. Normally, after carrying out the sterilization, the packaging is cooled (preferably still within an autoclave). Steam may condense inside the packaging during cooling. The steam condensed in the packaging cannot escape from the packaging in its liquid state, since the material of the second sub-section of the packaging, which is permeable to steam and possibly to other gases, is substantially not permeable to water in its liquid form. In principle, if necessary or desired, steam can escape or be released from the packaging before the second sealing, which can be used to keep the liquid water content in the final product or finished product low.

The time that is required for sterilization according to the method presented here is thus significantly shorter than when (as in the aforementioned disclosures) working with a pre-sealed volume.

Moreover, different packaging volumes are no obstacle to a fast, and efficient course of the method. Since the relative humidity of the atmosphere is adjusted, each packaging is essentially given humidity in proportion to its size or volume. It is not necessary to adjust the dose of water or the quantity of water to the size of the packaging.

During the first sealing step, a single contiguous spatial area is created. This is delimited from the environment by means of the packaging, which consists of at least the two different materials mentioned. This interior space contains the material to be treated, which is to say, the intraocular lens, for example, alone or with the injector and/or loading chamber, in particular preferably the intraocular lens is preloaded in the loading chamber of the injector and thus contained in the packaging with the injector. By means of the second sealing step, the aforementioned single contiguous spatial area is divided into two spatial areas, whereby the first spatial area, in which the material to be treated remains, is preferably several times larger, in particular at least three times larger, than the second spatial area, which can be detached if necessary.

The packaging has a reduced interior space after the second sealing, which interior space is smaller than the original interior space after the first sealing.

Water that has entered the interior space as steam during sterilization may be enclosed in the packaging after the second sealing. No additional water actually needs to be introduced into the packaging for further storage of the intraocular lens in the finished packaging. The water introduced during sterilization and still remaining in the packaging after the second sealing is, in principle, sufficient to store the intraocular lens in wet conditions. However, since hardly any material and therefore hardly any packaging is one hundred percent impermeable to water or steam, it can nonetheless be useful to add additional water before the first sealing, so to speak as a reserve, so that the product remains sufficiently humid notwithstanding packaging material-related loss of water over the course of its entire storage time period, which can be several years.

Preferably, when speaking of sterilization, this is at least one steam sterilization.

For sterilization, the packaging sealed according to the first sealing is expediently exposed to an atmosphere with a certain humidity for a certain period of time, which is to say, for the duration of the actual sterilization cycle, such that the humidity can penetrate through the second sub-section into the interior space of the packaging in order to increase the humidity in the interior space.

The duration of the actual sterilization cycle is defined, in particular, by the time period during which the temperature is within a predefined range or at a predefined value.

In particular, the packaging sealed according to the first sealing is exposed for a certain period of time to an atmosphere with a relative humidity of at least 90%, preferably a steam saturated atmosphere. In this, the temperature is preferably 100° C. (Celsius) or higher, more preferably 110° C. or higher, more preferably 120° C. or higher.

The certain period of time is at a temperature in the range of 100° C. to 130° C., in particular at 121° C., preferably up to 30 minutes, further preferably up to 25 minutes, and particularly preferably about 20 minutes. At a temperature in the range of more than 130° C., in particular at 134° C., the certain period of time is preferably up to 15 minutes, further preferably up to 10 minutes and particularly preferably 5 minutes.

The sterilization is expediently carried out in an autoclave or in its treatment chamber. The method enables safe sterilization, which [can be performed] in commercially available autoclaves using standard sterilization parameters.

For better protection of the intraocular lens, the intraocular lens is preferably placed in the packaging together with a holder, in particular wherein the intraocular lens is inserted into the holder. Instead of a random holder, a loading chamber can be used in which the intraocular lens is preloaded. The loading chamber can be designed as a cartridge which can be inserted into an injector or can be integrated into an injector.

The method is advantageously characterized in that the intraocular lens is preloaded together with a holder, in particular inserted in the holder, and/or a loading chamber, in particular preloaded in the loading chamber, and/or an injector, in particular preloaded in the injector, is inserted into the packaging, and the intraocular lens together with the holder, the loading chamber and/or the injector is enclosed in a liquid-tight manner in the packaging by the first sealing, is sterilized and is enclosed in a gas-tight manner in the packaging by the second sealing. The method allows lenses, that are normally stored in liquid, to be stored exclusively in water-saturated air without drying out and becoming damaged.

In addition to steam, other gaseous sterilizing substances may optionally be used, in particular, those selected from the group consisting of ethylene oxide, formaldehyde, ozone, hydrogen peroxide and combinations thereof, with ethylene oxide being preferred.

The second sub-section advantageously consists, at least partially, of material which is permeable to steam and possibly other gaseous sterilizing substances, but which is impermeable to liquid water. For example, the second sub-section consists at least partially of PE-HD (high density polyethylene). The PE-HD is preferably made of PE-HD-nonwoven fabric by an evaporation spunbond process. Alternatively, any other packaging material commonly used for autoclaving can be used, such as, for example, medical autoclave paper, provided it is permeable to steam and possibly other gaseous sterilizing substances, but impermeable to liquid water.

After the second sealing step, the portion of the packaging that includes the second sub-section and which does not form the now reduced interior space is expediently optionally detached and discarded.

The second sub-section preferably constitutes an end area of the packaging so that it can be detached as easily as possible after it is no longer needed.

The invention further relates to a lens pack containing an intraocular lens in a packaging, preferably the intraocular lens is stored in a holder or preloaded in a loading chamber and/or in an injector, wherein the packaging forms a sealed, in particular gas-tight, interior space in which the intraocular lens is contained, optionally with holder, loading chamber and/or injector.

Insofar as the lens pack contains, in addition to an intraocular lens, an injector, in particular in or on which the intraocular lens is placed, this is also called an injector pack. A first embodiment of the lens pack or of the injector pack, which, in particular, can be autoclaved, is advantageously characterized in that the packaging has two sub-sections, a first sub-section, which defines a first interior space area, in which the intraocular lens, optionally with holder, loading chamber and/or injector, is placed, and a second sub-section which defines a second interior space area, wherein the second sub-section has a window made of steam permeable material which may also, optionally, be permeable to other gases, wherein volumes of the two interior space areas are connected to one another and wherein, in a transition area between the two interior space areas, a structure, for example, a cross-piece, is formed, which structure is provided for sealing, for example, by welding or bonding, so that the two interior space areas can be separated from one another in a gas-tight manner by welding. It should be noted that the packaging material, with the exception of the window of steam permeable or gas permeable material, is substantially impermeable to gas or is gas-tight. This first embodiment (comprising two sub-sections which form one cohesive volume) may also be referred to in a functionally descriptive manner as a lens pack semi-finished product that can be autoclaved.

In the first embodiment, the lens pack that can be autoclaved is, in particular, characterized in that the packaging is designed in such a way that the first sub-section, which is filled with the intraocular lens and, optionally, with the holder, loading chamber and/or injector, can be sealed off from the second sub-section, namely sealed in a gas-tight and liquid-tight manner.

Preferably, at least on one of the two sub-sections, preferably on the second sub-section, one or more further structures can be formed which are shaped in such a way that a passage between the first and second sub-sections of the packaging is kept free to ensure gas exchange between the first and second interior space areas. In particular, a closing of the passage by collapsing of the packaging, in particular before or during sterilization, is to be prevented. The one or more further structures can expediently be formed on the inside of the packaging so that the packaging cannot collapse on itself. In this way, a gas exchange of the entire interior space of the packaging can be ensured during a sterilization treatment. This one or more further structures are expediently elevated relative to the cross-piece so that the packaging cannot collapse (especially not without external action) into itself or fall onto the first-mentioned structure or the cross-piece structure.

The lens pack, or alternatively the injector pack, according to a second embodiment is advantageously characterized in that the packaging comprises two sub-sections, a first sub-section which defines a first interior space area, in which the intraocular lens, optionally, with holder, loading chamber and/or injector can be placed, and a second sub-section which defines a second interior space area, wherein the second sub-section has a window made of steam permeable material which may optionally also be permeable to other gases, wherein the volumes of the two interior space areas are separated from one another by a sealing, in particular a welding or bonding together of the packaging material. For the purpose of manufacturing the second embodiment, the welding together is carried out following autoclaving. Therefore, this second embodiment of the lens pack may also be referred to in a functionally descriptive manner as an autoclaved (or sterilized) and sealed lens pack (or, in contrast to the first embodiment, also as a lens pack finished product), which includes the lens in a first sub-section that is sealed off from the second sub-section after autoclaving.

In a concrete example, the lens pack according to the first or second embodiment may be implemented as a packaging pouch, wherein the pouch comprises at least a first interior space area in which the lens (or the lens stored in a holder, a loading chamber or an injector) is accommodated, and at least a second interior space area, wherein the window is formed in an area of the packaging pouch which forms the second interior space area (but not the first interior space area), and wherein the second interior space area can be clamped off from the first interior space area occupied by the lens (or the lens stored in its holder, its loading chamber or its injector) and thereby the first interior space area can be sealed off in a gas-tight manner from the second interior space area and from the environment. This example is referred to hereinafter as the pouch design.

In the pouch design, the lens or the loading chamber or the injector in which the lens is stored or preloaded is expediently fastened on a holder. The lens is thus carried by and in its holder in the packaging pouch. This holder ensures that the lens in the gas-tight sealed packaging pouch is spaced away from the packaging pouch material all around, in such a way that, as best as possible, the entire lens surface is in direct contact with the inner packaging atmosphere (and is thus not sealed off from the inner packaging atmosphere by direct contact with the packaging material).

The lens pack according to the first or second embodiment is characterized, in a preferred example, in that the packaging is formed of a container with a cover, wherein the container has a circumferential edge against which the cover can or does seal the container, and wherein the container expediently has at least one first depression which delimits or defines the first interior space area, and at least one second depression which delimits or defines the second interior space area, and wherein the window is formed in an area of the cover which covers up the second interior space area.

The aforementioned welding together used for separation of the volumes of the two interior space areas is expediently formed between the cross-piece and the cover.

In a first sub-section, the cover is expediently substantially gas-tight and steam-tight, and in a second sub-section, it is expediently permeable to steam and, optionally, gaseous sterilizing substances.

The lens pack is further advantageously characterized in that the packaging as a whole is watertight (which is to say, impermeable to liquid water). That is, the second sub-section, which is permeable to steam, is also impermeable to water, which is to say, liquid water.

The lens pack is advantageously characterized in that a cross-piece is formed in the container, which cross-piece separates the first sub-section from the second sub-section (or marks a line for a division into a first and second sub-section) and can preferably be substantially co-planar relative to a circumferential edge of the container (or substantially planar together with a circumferential edge of the container), which facilitates simultaneous or sequential welding of the container to a cover along the circumferential container edge and (thereinafter, if desired) along the cross-piece. That is, sealable surfaces on the container edge and the cross-piece are preferably co-planar (which is to say, lying on the same plane). The cross-piece expediently leads from a first location of the circumferential container edge to a second location of the circumferential container edge, preferably in a straight line. The two locations are, in particular, spaced apart one from the other.

To ensure a gas exchange between the first and second sub-sections, a structure is preferably formed in the first and/or second sub-section, preferably near the cross-piece, that is elevated relative to the cross-piece or relative to the co-planar surface of the cross-piece and the edge, which raises a cover that is to be fastened or is fixed to the circumferential edge of the container above the cross-piece, in particular, above the substantially co-planar surface of the cross-piece and the edge, such that a passage between the first sub-section and the second sub-section remains free between the cross-piece and the cover for the purpose of gas exchange. The elevated structure may, for example, be realized as one or more elevations in the first and/or second sub-sections. When speaking of the circumferential edge of the container, this means, in particular, the edge which runs around the first and the second sub-section. The cover is, for example, formed as a cover film, which is preferably fastened or can be fastened, or alternatively sealed or able to be sealed in an elastic manner and/or loosely or slackly hanging onto the circumferential edge, so that a subsequent fastening or sealing with the cross-piece is possible. The elevated structure is expediently formed on the inside of the packaging so that the packaging cannot collapse, in particular the cover cannot collapse.

To the extent that the expression 'preferably near the cross-piece' is used in relation to one or more elevated structures, the expression is, in particular, meant to convey that the respective elevated structure has a position which is characterized in that, on an imaginary plane, which is defined by the circumferential edge, the smallest distance between the position of the elevated structure and the cross-piece is smaller, several magnitudes smaller, than the distance from the elevated structure to the circumferential edge measured in an extension of an imaginary straight line indicating the aforementioned minimum distance on the plane of the circumferential edge.

In the pouch design, the gas exchange between the first and second interior areas of the pouch is ensured in that the lens, or the loading chamber, or the injector with lens, is placed in a holder which is pushed into the pouch. If the pouch is peripherally sealed off, which is to say, at the circumferential edge, then the holder can be slid into the second interior area where the window is located. This second interior area is made smaller or shorter than the holder. The holder thus protrudes into both the first and the second interior area and keeps the transition area between the two areas open during autoclaving. Prior to sealing in order to separate the two interior areas, the holder with the lens that it supports slides completely back into the first interior area of the packaging pouch.

Said packaging is, for example, manufactured of a film material. Preferably, at least the cover of said packaging is made of aluminum, in particular of aluminum foil, wherein, however, the window of the cover as described herein, to the extent it is present, consists of another material, namely a gas permeable material.

Further disclosed is a lens pack or injector pack containing an intraocular lens, which is optionally preloaded in an injector, and a packaging for enclosing the intraocular lens and injector, wherein the packaging forms a sealed interior area, in particular a gas-tight sealed interior space in which the intraocular lens is contained, optionally with the injector, wherein the lens pack or injector pack is characterized in that the packaging seals the interior space in a gas-tight manner and in that a sterilized gas atmosphere containing steam is present in the interior space. It can also be said that the sterilized gas atmosphere consists substantially of humid air. This lens pack or injector pack can be referred to as a finished product. The finished product has a sterilized gas-tight interior space in which an intraocular lens is stored, in particular, stored wet.

The packaging may have a cut edge outside the sealed interior space, indicating that a second portion of the packaging, which was important in creating the gas atmosphere but is no longer useful in the finished product, has been detached. This means disclosure of a lens pack or injector pack, in particular a lens pack finished product or injector pack finished product, containing an intraocular lens in a packaging, preferably the intraocular lens stored in a holder or preloaded in a loading chamber and/or in an injector, wherein the packaging forms a sealed interior space in which the intraocular lens, optionally with holder, loading chamber and/or injector is contained, in which the packaging defines an interior space area in which the intraocular lens is stored, optionally with holder, loading chamber and/or injector, wherein the volume of the interior space area is sealed off from the environment by a sealing, in particular a welding or bonding, of the packaging material, and outside of the sealed interior space has a cut edge or breaking edge at the edge of the sealing, in particular the welding or bonding.

Preferably, the sterilized gas atmosphere is saturated with steam. In particular, the internal atmosphere is steam saturated at room temperature (in particular at 20° C.) and normal pressure (which is to say, 1 atm=1013.25 mbar=101.325 kPa), particularly preferably at least in the temperature range from RT to 30° C., more preferably from RT to 40° C., more preferably from RT to 50° C., more preferably from RT to 60° C., more preferably from RT to 120° C.

The packaging material, in particular the container and the cover, excluding the window material, to the extent that it is present, preferably has a steam permeability of less than 10 g/m²/24 h, preferably less than 1 g/m²/24 h and more preferably less than 0.1 g/m²/24 h.

The packaging material, in particular the container, preferably has a wall thickness of more than 0.4 mm, further preferably more than 0.6 mm, further preferably more than 0.8 mm. The packaging material having these wall thicknesses can, for example, be made of a plastic.

The packaging material, in particular the container is dimensionally stable. The dimensionally stable packaging material can, for example, be made of a plastic.

The packaging material, in particular the container, may be made of a plastic, in particular, for example, polypropylene (PP), polyethylene terephthalate (PET) or a combination thereof.

Preferably, the packaging of the lens pack or injector pack forms a single packaging.

Alternatively, the packaging of the lens pack or of the injector pack may form the innermost packaging of a combination packaging. That is, a second sterile packaging (for example, a sterilization pouch) is arranged around the previously described single packaging used as the primary packaging, so that the exterior of the primary packaging is also sterile after autoclaving.

Part of the packaging is preferably designed to receive the injector in one or more clamping grips and thereby fasten it in place. This makes an additional holder for fastening the injector in position within the packaging superfluous.

The interior space of the injector pack expediently contains a single injector, which is thus sterilized and ready for single use in an eye operation.

The injector in the injector pack expediently contains an intraocular lens, preferably an intraocular lens inserted or preloaded in the injector or in the loading chamber of the injector.

The intraocular lens is preferably a hydrophilic intraocular lens. A hydrophilic intraocular lens is advantageously stored in a relaxed state in the injector.

The gas atmosphere in the lens pack or injector pack can be generated according to the method described herein. The sterilized gas atmosphere is preferably a steam-sterilized and/or EtO-sterilized gas atmosphere, wherein a steam-sterilized gas atmosphere is particularly preferred for hydrophilic intraocular lenses. The sterilized gas atmosphere in the packaging or in the interior space of the packaging shell is, in particular, air containing steam (preferably steam saturated air), which has been generated by introducing hot steam, in particular of 100° C. or more, preferably 110° C. or more, more preferably 120° C. or more, more preferably 130° C. or more.

To the extent that a lens pack includes an injector on which the intraocular lens is preloaded, the lens pack is also referred to as an injector pack.

A packaging for an intraocular lens is also disclosed. Such a packaging expediently has an interior space which is suitable for receiving an intraocular lens, in particular with or without a holder, preloaded in a loading chamber or preloaded in an injector. In particular, the packaging has two sub-sections, a first sub-section which defines a first interior space area, into which an intraocular lens, optionally with or without a holder, loading chamber and/or injector, can be inserted, and a second sub-section which defines a second interior space area, wherein the second sub-section has a window made of gas permeable, in particular steam permeable, material, wherein the volumes of the two interior space areas are connected to each other and wherein a structure, for example, a cross-piece, is formed on the packaging in a transition area between the two interior space areas, which structure is provided for sealing, for example, by welding or bonding, so that the two interior space areas can be separated from one another in a gas-tight manner by sealing, in particular by welding or bonding. The packaging may—to the extent that it is relevant—have further features or combinations of features as described herein also with respect to a lens pack or injector pack. The packaging may be used, in particular, in the described method.

The optional features mentioned may be implemented in any combination, provided they are not mutually exclusive. In particular, where preferred ranges are indicated, further preferred ranges result from combinations of the minimum and maximum values mentioned in the ranges.

A particularly advantageous aspect of the packaging method presented above is that the packaging steps lead to a lens pack semi-finished product, in particular an injector pack semi-finished product, which provides an intraocular lens in a packaging within which the lens is enclosed in a liquid-tight but not gas-tight manner, so that the contents of the packaging can still be sterilized through the introduction of gas and then sealed in an airtight manner. The lens pack semi-finished product or injector pack semi-finished product is, in particular, manufactured in said process and further processed to an injector pack finished product.

Further advantages, features and preferred embodiments of the invention will be apparent from the following detailed description of the invention with reference to figures.

BRIEF DESCRIPTION OF THE FIGURES

The figures are schematic representations that are not to scale:

FIG. 3: Shows a side view of the container according to FIG. 1;

FIG. 4: Shows a front view of the container according to FIG. 1;

FIG. 5: Shows a top view looking down on the container according to FIG. 1;

FIG. 6: Shows a top view looking down on a cover film (without container);

The invention is hereinafter described in more detail with reference to the figures. The preferred features mentioned can be realized in any combination, provided that they are not mutually exclusive.

In the following, the same reference numbers stand for the same or functionally identical elements (in different figures).

DETAILED DESCRIPTION OF THE FIGURES

Figure 1:
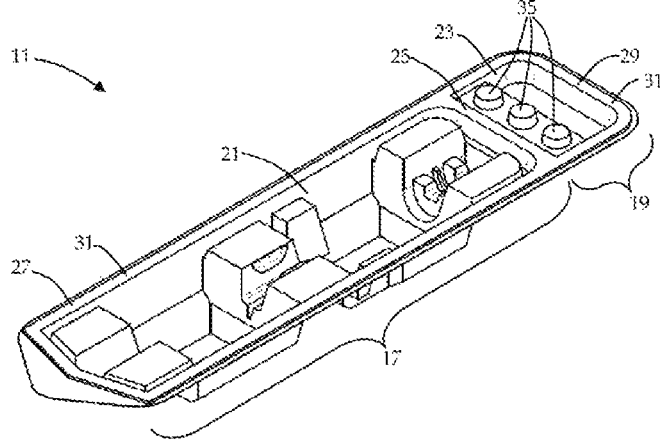
FIG. 1: Shows an oblique perspective view of the container (oblique from above) without cover.
Figure 2:
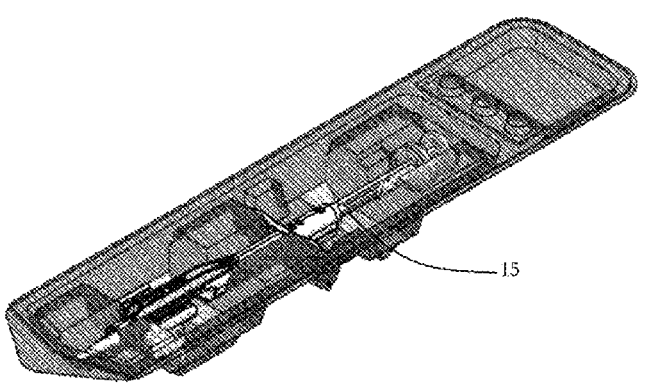
FIG. 2: Shows an oblique perspective view of a container with an injector inserted therein with a loaded loading chamber.

FIG. 1 shows a container 11 that is used to hold a preloaded injector. FIG. 3 and FIG. 4 each show a side view of the container 11. FIG. 5 shows a top view looking down on the container 11. The container 11 can be sealed with a cover 13, as shown in FIG. 6. The container 11 and cover 13 form a packaging for enclosing an injector 15 preloaded with an intraocular lens. A container 11 into which an injector 15 is inserted is shown in FIG. 2. The container 11 is expediently designed in such a way that an injector can be precisely inserted and is preferably lightly clamped at least at one point, so that the injector does not slip in the container, for example even when the container is turned upside down. The packaging loaded with the preloaded injector 15 may generally be referred to as an injector pack or, more generally, a lens pack.

The packaging substantially has two sub-sections, namely a first sub-section 17 and a second sub-section 19. The two sub-sections are substantially defined by the shape of the container 11 and a made to match cover 13. On the container side, the first sub-section 17 is defined by a first depression 21 of the container 11 and the second sub-section 19 by a second depression 23 of the container 11, the two depressions being delimited from each other by a cross-piece 25. The breakdown into the first and second sub-sections 17 and 19 is readily visible in FIG. 3 due to the separation of the two depressions 21 and 23 by the cross-piece 25. Each of the two depressions 21 and 23 is delimited by the respective portion 27 or 29 of the circumferential container edge 31, which extends all the way to the cross-piece 25, and also delimits the cross-piece 25 itself. On the cover side, the first sub-section 17 is defined by that portion of the cover 13 which covers the first depression 21. The second sub-section 19 is defined on the cover side by that portion of the cover 13 which covers the second depression 23.

The packaging material in the first sub-section 17 is characterized in that it consists of a substantially gas-tight material, whereas the packaging material in the second sub-section 19 is characterized in that it consists at least in part of a gas permeable material, in particular a steam permeable material, but preferably at the same time substantially acts as a seal against liquids. The cover 13 is, in particular, made in part of a gas permeable material. The cover 13 has an area of gas permeable material, in particular, over the second sub-section 19, whereas the remainder of the cover 13 is made of substantially gas tight material.

The container 11 is preferably made of a substantially dimensionally stable material in order to provide support for the packaged goods and to enclose the packaged goods in a manner that is shock resistant to the environment. The container can be shaped, for example, by a deep-drawing process. The container 11 is expediently made of a substantially gas-tight material, in particular, inasmuch as the cover 13 has an area of gas permeable material. The cover 13 may be made of foil material. The foil material may be thin enough to allow the cover to be bent so that the cover 13 can easily be pulled away from the container 11.

In the embodiment shown in FIG. 1 and FIG. 6, the container 11, in a preferred manner, consists substantially, for example, of a plastic with the lowest possible gas permeability and/or aluminum. The container material should substantially only allow as minimal a gas exchange as possible between the interior space of the packaging and the external environment, in particular, for example, it should not allow any exchange of air and steam. To the extent that a plastic is used as packaging material, polypropylene may, for example, be used. Polypropylene packaging material preferably has a thickness or wall thickness of >0.4 mm, preferably >0.6 mm, further preferably >0.8 mm.

The cover 13 is likewise, to a large extent, made of a gas-tight material, for example, gas-tight plastic and/or gas-tight aluminum, in particular a gas-tight plastic and/or aluminum foil. However, the cover 13 has a type of window 33 in one area which is made of a gas permeable, in particular air and steam permeable, material. This gas permeable area 33 of the cover 13 is provided in the second sub-section 19 of the packaging, preferably on the cover side in the second sub-section 19 of the packaging, which is to say, in the cover 13 and specifically in that part of the cover 13 which covers the second depression 23. Alternatively or additionally, such a gas permeable area could also be formed in the container portion of the second sub-section 19.

The cross-piece 25 of the container 11 separates the first depression 21 from the second depression 23 and preferably forms a plane which is substantially co-planar in relation to the circumferential edge 31 of the container 11.

The co-planar surfaces of the circumferential edge 31 and the cross-piece 25 are suitable for welding or bonding to the cover 13. In particular, the material of the container 11 and the cover 13 is preferably selected such that welding is possible.

In the second sub-section 19, one or more elevations 35 are formed, which preferably project beyond the plane defined by the circumferential edge 31 of the container 11 and the cross-piece 25. The elevations 35 should at least project above the nearby cross-piece 25 (or the elevations 35 should be formed higher than the cross-piece 25, if for example, the circumferential edge 31 is considered as reference plane) and in such a way that, due to the projecting elevations, a passage for the exchange of gas between first and second sub-sections is kept free between the cross-piece 25 and the cover if the cover is fastened on or welded or bonded to the circumferential edge 31. In so doing, the elevations 35 may protrude from the second depression 23; however, this is not mandatory but is nonetheless advantageous for the provision of an exchange of gas. The elevations 35 may, in particular, be cylindrical or frustoconical in shape. It is advantageous, for example, to have a design with at least two or three elevations 35 arranged parallel to each other. The elevations 35 preferably define a common elevation and/or originate from a common plane. Further preferably, any two adjacent elevations are spaced no further apart than they are wide in the direction of their shortest connecting line. Preferably, therefore, the cover 13 should not be able to sag onto the cross-piece 25 by itself or due to gravity alone. The cover is designed, for example, as a cover film, which is preferably elastic and/or loosely or slackly suspended on the circumferential edge such that, notwithstanding the elevations, a subsequent fastening or sealing of the cover 13 to the cross-piece 25 is possible by pressing the cover 13 onto the cross-piece 25.

After the container 11 and the cover 13 are shown and described separately, they are described in the following description in combined versions according to FIG. 7 and FIG. 8. In this, analogous parts are provided with the same reference signs, so that a further detailed description of the analogous parts is unnecessary, or alternatively reference is made to the analogous parts already described using unchanged reference signs.

Figure 7:
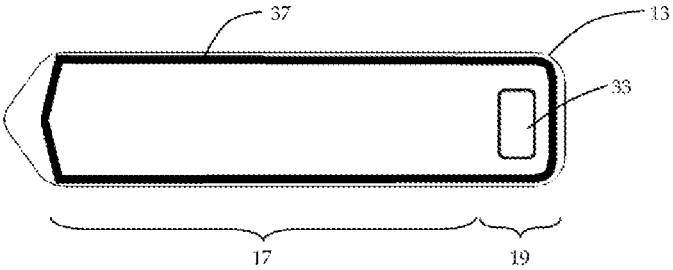
FIG. 7: Shows a top view looking down on a container covered with cover film, with indication of the location of sealing seams between the container and the cover film, wherein the container is continuously sealed along its edge with the cover film.

FIG. 7 shows a top view looking down on a container 11 which is covered with cover film 13. Marking 37 indicates the position of a sealing seam between container 11 and cover film 13, wherein the container 11 is continuously sealed along its circumferential edge with cover film 13. The packaging has two sub-sections, a first sub-section 17 defining a first interior space area in which the intraocular lens is stored, optionally with holder, loading chamber and/or injector, and a second sub-section 19 defining a second interior space area. The second sub-section 19 has a window 33 of steam permeable material. Since no weld seam is indicated above the cross-piece 25 (not visible in FIG. 7), the volumes of the two interior space areas are connected to each other. The first interior space area corresponds approximately to the first depression 21 and the second interior space area corresponds approximately to the second depression 23. Each of the two interior space areas, which are in fact measured up to the cover, has a slightly increased volume compared to the respective depression, which is, in principle, only measured up to the level of the seam, since the elevations 35 raise the cover 13 above the cross-piece 25 or above the common level of the circumferential edge and cross-piece. The cross-piece 25, which is formed in the transition area between the two depressions, is provided for performing a second welding step, such that by performing the second welding step, the two interior space areas can be separated from each other in a gas-tight manner.

The packaging as a whole is thus designed in such a way that a first sub-section 17 made of gas-tight material, which contains the intraocular lens (optionally intraocular lens with holder, loading chamber and/or injector), can be sealed with respect to a second sub-section 19, which is watertight but not gas-tight (but permeable to gas and steam). As a consequence, the contents of the packaging (which is to say, the intraocular lens, possibly with holder, loading chamber and/or injector) can be sterilized by gas, in particular can be steam sterilized. In this embodiment, the packaging may be referred to as a lens pack semi-finished product or, to the extent that the lens is preloaded in an injector, as an injector pack semi-finished product, or also as a lens pack or injector pack that can be sterilized by gas or by steam. The semi-finished product is characterized in that, in particular, the packaging is divided into a first sub-section 17 and a second sub-section 19, wherein the sub-sections form a common volume space and wherein the first sub-section 17 of the packaging is made of gas-tight material and contains the lens or the injector with lens preloaded therein, whereas the second sub-section 19 of the packaging, which may be made of the same material, has at least a portion which is made of a gas permeable material, in particular, for example, steam permeable material. This portion of the packaging made of gas permeable, in particular steam permeable material, is also referred to herein as window 33. Advantageously, due to the steam permeable window 33, the packaging or the packaging interior space can be sterilized with steam in a sealed state or optionally with another gas by allowing steam and/or another suitable gas to flow in through the steam or gas permeable window before or during sterilization. The sterilization can, for example, be carried out in an autoclave, in which the composition of the atmosphere, the pressure and/or the temperature can preferably be predetermined and, if necessary, controlled. The packaging is sealed as a whole with respect to liquids, which is to say, the packaging is watertight (which is to say, impermeable to liquid water). A sterilization by means of EtO gas is therefore likewise possible.

The second sub-section 19 preferably constitutes an end area of the packaging. In this context, the term end area is to be understood as meaning that the second sub-section 19 is arranged in the packaging in such a way that this second sub-section 19 or its inner volume can be separated or detached from the first sub-section 17 or its inner volume as easily as possible by clamping or cutting (for example in the second sealing step). For example, if the packaging including the first sub-section and the second sub-section has an elongated shape as a whole, the second sub-section 19 shall be provided at one of the two ends of the elongated shape, as can be seen in the embodiment example shown in the figures (in particular, FIG. 1 or one of FIG. 3 or 5-9). In an elongated packaging form similar to that shown in the figures, the two ends (and thus the two sub-sections) can be separated from each other by clamping or cutting perpendicular to the longitudinal extension.

Excluding the steam permeable or gas permeable window 33 of the cover, it is possible for the cover 13 of the packaging to be made of aluminum, in particular aluminum foil. The steam permeable or gas permeable window 33 may be made of a non-woven fabric of high density polyethylene (PE-HD) (for example, Tyvek®) or also of (ordinary) autoclave paper. The container 11 can be made of a low-cost plastic with preferably low steam permeability (for example, polypropylene or plastic with an EVOH (ethylene vinyl alcohol copolymer) layer, in particular plastic with an extruded EVOH middle layer).

Figure 8:
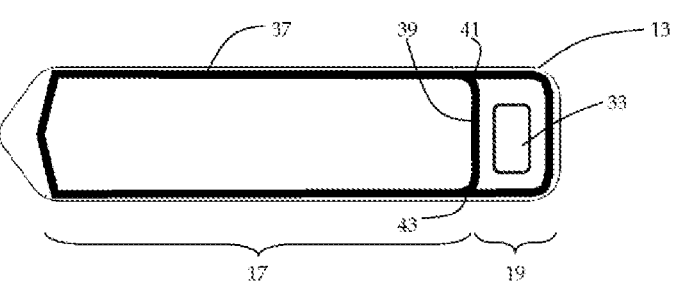
FIG. 8: Shows a top view looking down on a container covered with cover film, with indication of the location of sealing seams between the container and the cover film, wherein the container, as in FIG. 7, is sealed along its edge with the cover film and additionally over a cross-piece with the cover film.
Figure 9:
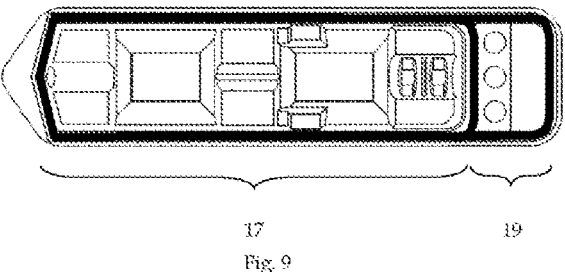
FIG. 9: Shows a top view looking down on a container with indication of the planned location of sealing seams between the container and a cover film.

FIG. 8 also shows a top view looking down on a container 11 covered with cover film 13. As already mentioned, the packaging has two sub-sections, a first sub-section 17, which defines a first interior space area, in which the intraocular lens is stored, possibly with holder, loading chamber and/or injector, and a second sub-section 19, which defines a second interior space area. In FIG. 8, in contrast to the packaging version in FIG. 7, between container 11 and cover film 13, there is a marking 39 of the position of an additional sealing seam running over the cross-piece 25, this in addition to the marking 37 of a sealing seam running around the edge. Which is to say, whereas the packaging design according to FIG. 7 has a continuous overall interior space that is made up of the first interior space area of the first sub-section 17 and a second interior space area of the second sub-section 19, the packaging design according to FIG. 8 has an additional sealing seam section (see marking 39) running between two locations, which is to say, a first location 41 and a second location 43 of the circumferential sealing seam (see marking 37), which divides (or separates) said first interior space from said second interior space, so that the first interior space is separated from the surroundings and from the second interior space in a substantially steam-tight or gas-tight manner. The additional sealing seam (see marking 39) extends from the first location 41 of the circumferential sealing seam (see marking 37) along the cross-piece 25 to the second location 43 of the circumferential sealing seam. The additional sealing seam, which is indicated by the marking 39 in FIG. 8, thereby separates the volumes of the two interior space areas from each other. The sealing between the cross-piece 25 of the container 11 and the cover film 13 is carried out, for example, by heat welding or bonding. The first sub-section 17 of the packaging forms (after sealing over the cross-piece) a gas-tight sealed lens pack or injector pack. The second sub-section 19 of the pack is now redundant and can be detached if necessary, for example, cut off using a cutting instrument, and discarded. The gas-tight sealed lens pack or injector pack is, so to speak, the end product or finished product.

Figure 10:
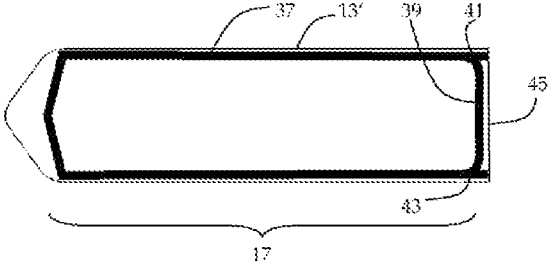
FIG. 10 Shows a top view looking down on a container covered with cover film with indication of the location of sealing seams between the container and the cover film, wherein the container is sealed along its edge with the cover film, wherein the container has a cut edge on a side outside the sealing seam.

FIG. 10 shows such a lens pack or injector pack finished product. The pack has a cut edge 45 outside the gas-tight sealed interior space, which consists essentially of the depression 21, which is to say, outside the first sub-section 17 of the pack. The cut edges are substantially formed by separating the second sub-section 19 or the larger portion of the second sub-section 19 from the first sub-section 17, in particular by separating the sub-section 19 containing the gas permeable window 33. The cut edge 45 expediently runs substantially along or near or even in the bonding or welding line 39, which is arranged between the cut edge 45 and the sealed interior space, which is to say, on the cross-piece 25. In particular, the cut edge 45 extends through the original container 11 as well as through the original cover 13 attached to the container in such a way that the remaining container portion and cover portion 13' can be described as shortened compared to the original shape of the container and cover.

The injector pack comprises an injector 15 with an intraocular lens and a packaging for enclosing the injector and intraocular lens, wherein the gas-tight or steam-tight packaging forms a sealed gas-tight or steam-tight envelope which defines an interior space in which the injector 15 with intraocular lens is contained, wherein a sterilized gas atmosphere containing steam is present in the enclosed interior space.

The injector pack, as shown, for example, in FIGS. 1-9, therefore preferably consists at least of a steam-tight or gas-tight packaging of a container with cover (steam-tight or gas-tight container and cover), wherein the container has at least one depression with a holding structure for holding or clamping the injector and the cover covers the depression with the injector stored therein. In said injector pack, the injector is sealed from the environment in a gas-tight manner.

Figure 11:
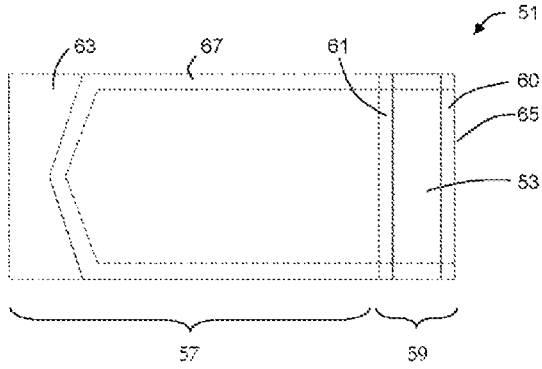
FIG. 11 Shows a pouch with gas permeable area and sealing strip.

In an alternative and simplified embodiment, as shown in FIG. 11, the packaging for an intraocular lens to be stored in a wet state can be designed as a pouch 51, which has a gas permeable or steam permeable window 53 but otherwise consists of a material that is impermeable to gas and steam. The pouch 51 is designed, for example, as a relatively flat structure with an opening 65 at a side edge of the pouch. The gas permeable or steam permeable window 53 is arranged, for example, near the opening 65. Due to the location of the gas permeable or steam permeable window 53 near the opening 65, and thus near an edge of the flat structure, it follows that the pouch is formed from a first sub-section 57 that is impermeable to gas and steam and a second sub-section 59 that is permeable to gas and steam. The pouch 51 has two strips 60 and 61 provided for sealing the pouch. The sealing strips may be coated with sealable or bondable material, on the basis of which the pouch surfaces bond and thereby allows the pouch interior space to be sealed off gas-tight from the environment. The first strip 60 is preferably arranged along the pouch opening 65. The second strip 61 is expediently spaced away from the first strip 60 and in comparison to the first strip 60 is spaced at a greater distance from the pouch opening 65. Both sealing strips preferably extend in a substantially straight line from one edge of the pouch to the opposite edge of the pouch and also parallel to the pouch opening 65. The sealing strips 60 and 61 may thereby be oriented parallel to each other. The gas or steam permeable window 53 is formed between the sealing strips. At least the second sealing strip 61 is applied in the material that is impermeable to gas and steam. The pouch 51 or its interior space can be sealed off from the environment by means of the first sealing strip 60. The pouch contents that are contained in the pouch sealed in this manner can be sterilized by introducing hot steam through the window for sterilization. By means of the second sealing strip 61, the first sub-section 57 that is impermeable to gas and steam can be separated in a gas-tight manner from the second sub-section 59 which has the gas and steam permeable window 53. For this purpose the pouch contents are pushed into the first sub-section 57 of the pouch before the second sealing of the two sub-sections 57 and 59. The pouch is designed in such a way that an intraocular lens, which is preferably supported by a holder or preloaded in an injector or its loading chamber, can be inserted into it. The pouch, as a whole, as well as the sub-section 57 alone is designed to be at least large enough to accommodate an intraocular lens with holder or to be preloaded in the loading chamber and/or injector in the first sub-section 57 of the pouch 51 and not to hinder the sealing off of the first sub-section 57 from the second sub-section 59. The pouch further comprises a flap 63 by means of which the pouch can be opened when sealed, for example, at the second sealing strip 61. Seams or tear connections 67 that are expediently applied for this purpose tear open when pulling upon the flap 63.

In contrast to the flexible pouch 51 presented here in FIG. 11, a dimensionally stable container 11, as described with reference to figures from 1 to 10, additionally protects the contents against mechanical influences due to its dimensional stability, which can, in principle, be advantageous over a flexible pouch. However, it was determined during the development of the dimensionally stable container, that a dimensionally stable container, which on the one hand is rigid and on the other hand is designed in such a way that it allows a good exchange of gas during a sterilization treatment, cannot be separated from a gas permeable part and sealed as easily after the sterilization treatment as is possible with a flexible pouch. The preferred embodiment proposed here of the dimensionally stable container solves these problems by using a two-chamber system in which the sealing surfaces are substantially in a common plane and the gas can nevertheless flow freely from one chamber to the other during the sterilization treatment (which is to say, before sealing). In particular, it has been found that gas flow can be advantageously provided if the cover is designed to be flexible, in particular more flexible than the container.

The method for manufacturing a packaging with a sterile and substantially gas-tight intraocular lens enclosed therein, in particular a gas and/or steam sterilized gas-tight lens pack or injector pack, will be described here below. The manufacturing method includes the following sequence of steps:

Insertion of an intraocular lens (optionally with holder, loading chamber and/or injector 15) into an interior space of a packaging, wherein the packaging in a first sub-section 17 consists of a first packaging material which is substantially gas-tight, and in a second sub-section 19 includes a second packaging material which is permeable to gases, such as steam and optionally other gaseous sterilizing substances.

First sealing of the packaging so that the intraocular lens is enclosed within the interior space of the packaging, the interior space being partially bound or delimited from the surroundings by the first sub-section 17 and partially delimited by the second sub-section 19. The packaging is, in particular, substantially impermeable to liquids or solids.

Sterilization of the interior space of the packaging sealed according to the first sealing by exposing the packaging sealed according to the first sealing to steam and optionally other gaseous sterilizing substances for the purpose of sterilization, so that the steam and optionally the optional other gaseous sterilizing substances can penetrate into the interior space of the packaging through the second sub-section 19.

Second sealing of the packaging by sealing off at least a portion of the volume of the gas-tight first sub-section 17 of the packaging with the intraocular lens 15 enclosed therein from the volume of the second sub-section 19, whereby the intraocular lens 15 is completely packaged in the gas-tight first packaging material, which after the second sealing forms a reduced interior space that is smaller than the original interior space after the first sealing.

Preferably, a non-negligible portion of the water that has penetrated the interior space as steam during sterilization is still contained in the reduced interior space after the second sealing step, in particular so that the weight of the amount of water contained in the packaging (in particular, including vaporous water and possibly condensed liquid water) is greater after the second sealing step than it previously was after the first sealing step and before the start of sterilization.

The packaging sealed according to the first sealing step is exposed for sterilization to an atmosphere with a certain humidity for a certain period of time, so that the humidity can penetrate through the second sub-section 19 into the interior space of the packaging to increase the humidity in the interior space. In addition, the sterilization is preferably performed at a temperature that is higher than that of room temperature. It is particularly preferred that the sterilization step is carried out in an autoclave. For this purpose, the packaging is placed in a treatment chamber of the autoclave. An atmosphere with a relative humidity of at least 90% or, further preferably, a steam saturated atmosphere is set In the treatment chamber. At the same time, the temperature in the treatment chamber of the autoclave is set to preferably 100°

C. (Celsius) or higher, more preferably 110° C. or higher, more preferably 120° C. or higher. The sterilization can be performed under the aforementioned conditions (to atmosphere composition, humidity saturation and temperature) within a maximum of 30 minutes, preferably a maximum of 25 minutes, further preferably a maximum of 20 minutes.

Particularly preferably, the intraocular lens is preloaded in an injector. The injector is inserted into the packaging with the intraocular lens preloaded therein. In the cases described, the intraocular lens is placed in the packaging together with a holder, the loading chamber and/or the injector and enclosed in the packaging by the first or second sealing.

The second sub-section 19 consists at least partially of material which is permeable to steam and possibly other gaseous sterilizing substances, but which is impermeable to liquid water. In practical terms, a PE-HD nonwoven or autoclave paper is used.

The packaging, in particular packaging in the semi-finished product, is designed in such a way that (for example, after sterilization) the first sub-section 17 can be sealed off from the second sub-section 19 (for example, by pressing), so that the first sub-section 17, which contains the lens or the injector with preloaded lens, is thereby completely enclosed in the gas-tight material. This second sealing is carried out by welding or bonding the cover to the cross-piece 25.

A gas introduced into the first sub-section 17 during sterilization, or the gas contained in the first sub-section 17 at the end of the sterilization process, in particular, the steam preferably used for this purpose, can, to a large extent, be retained in the first sub-section 17 of the packaging after sterilization by sealing over the cross-piece 25 as quickly as possible.

After the second sealing step, the portion of the packaging containing the second sub-section 19 becomes redundant and can be removed if desired, for example, by cutting it off, and being discarded. Regardless of whether or not the sub-section 19 is removed after the second sealing step, the process described produces a lens pack that provides a sterilized intraocular lens packaged in a gas-tight manner. Preferably, the intraocular lens is preloaded in an injector, thereby providing an injector pack comprising a sterilized injector with the intraocular lens preloaded therein. Due to the introduction of humidity during sterilization, the interior space of the respective pack may have an atmosphere with a high degree of humidity. Preferably, this is (under equilibrium conditions) a steam saturated atmosphere.

The sterilized gas atmosphere of the injector pack consists essentially of humid air.

The sterilized gas atmosphere of the injector pack is advantageously saturated with steam, in particular, so that the intraocular lens does not dry out. It is expedient to have sufficient water (or sufficient water molecules) in the interior space of the injector pack so that the atmosphere in the injector pack is saturated with steam under conditions at room temperature (in particular, at 20° C.) and normal pressure (which is to say, 1 atm=1013.25 mbar=101.325 kPa). Preferably, sufficient water is present in the interior space of the injector pack so that, in particular, at normal pressure the gas atmosphere is saturated with steam at least in the temperature range from RT to 30° C., more preferably from RT to 40° C., more preferably from RT to 50° C., more preferably from RT to 60° C.

The packaging material of the injector pack suitably has a steam permeability of less than 10 $g/m^2/24$ h (for example, achievable with PET or PP), preferably less than 1. $g/m^2/24$ h and further preferably less than 0.1 $g/m^2/24$ h (for example, achievable with aluminum foil). A material or packaging that does not exceed this maximum steam permeability (0.5 $g/m^2/24$ h, preferably 0.05 $g/m^2/24$ h or further preferably 0.005 $g/m^2/24$ h) can be described as quasi gas-tight or steam-tight.

The packaging of the injector pack is a single pack. Alternatively, the described gas-tight or steam-tight packaging can form the innermost packaging of a combination packaging. In particular, the injector pack does not have an additional outer cover which has been autoclaved. The interior space of the injector pack expediently contains a single injector. The injector contains an intraocular lens, preferably an intraocular lens preloaded in the injector or in the loading chamber of the injector.

The intraocular lens is preferably a hydrophilic intraocular lens, because this type of lens benefits particularly from storage in a controlled humid environment. There are, however, also hydrophobic lenses with a slightly higher water content, which must also be stored in a controlled humid environment to prevent them from drying out. There is a consistently good shelf life due to the particularly well controlled or adjusted humidity conditions in the lens pack. This increases product safety.

The optics of the intraocular lens are preferably loaded in the injector in a relaxed state, which increases the shelf life of the injector pack or the lens.

The sterilized gas atmosphere in the injector pack is preferably a steam-sterilized gas atmosphere. Optionally, it can be a steam and EtO sterilized gas atmosphere. For hydrophilic intraocular lenses, a gas atmosphere sterilized only under steam is preferred.

Whereas specific embodiments have been described above, it is apparent that various combinations of the embodiments shown may also be used as long as the embodiments are not mutually exclusive.

Whereas the invention has been described above with reference to specific embodiments, it is apparent that changes, modifications, variations and combinations may be made without departing from the scope of the invention.

The invention claimed is:

1. A method for providing an intraocular lens enclosed in a packaging in a sterile and gas-tight manner, the packaging comprising a loading chamber with the intraocular lens preloaded therein or an injector with the intraocular lens preloaded therein, comprising the following:

inserting the intraocular lens into an interior space of the packaging, wherein the packaging, in a first sub-section defining a first interior space area that is configured for insertion of an intraocular lens and comprises a first packaging material that is gas-tight, and in a second sub-section defining a second interior space area and includes a second packaging material that is permeable to gas steam and gaseous sterilizing substances, but is impermeable to water in its liquid state;

first sealing of the packaging so that the intraocular lens is enclosed in the interior space of the packaging, the interior space being partly delimited by the first sub-section and partly delimited by the second sub-section;

sterilizing the interior space of the packaging sealed by the first sealing, by exposing the packaging to steam or a mixture of steam and other gaseous sterilizing substance, so that the steam or mixture of steam and gaseous sterilizing substance penetrates through the second sub-section into the interior space of the packaging;

cooling the packaging to condense at least some of the steam inside so that it cannot escape from the packaging;

second sealing of the packaging by sealing off at least one portion of the first sub-section of the packaging with the intraocular lens enclosed therein from the second sub-section so as to separate the first interior space area from the second interior space area in a gas-tight manner, whereby the intraocular lens and water that has penetrated as steam during sterilization is packaged within the first packaging material.

2. The method of claim 1, wherein during sterilizing the packaging is exposed to an atmosphere having a relative humidity of at least 90% and a temperature of at least 100° C.

3. The method of claim 2, wherein the sterilization of the packaging is in a temperature in a range of 100° C. to 130° C. for at least 20 minutes and at most 30 minutes or in a temperature in a range of 130° C. to 140° C. for at least 5 minutes and at most 15 minutes.

4. The method of claim 1, wherein the sterilization is carried out in an autoclave.

5. The method of claim 1, wherein the second sub-section comprises an end area of the packaging.

6. The method of claim 1, further comprising separating the second sub-section from the first sub-section.

7. The method of claim 6, wherein the separating the second sub-section from the first sub-section is by cutting or breaking.

8. The method of claim 7, wherein the packaging seals off at least a portion of the sealed interior space in a substantially gas-tight manner, and wherein an atmosphere containing the steam or the steam and other sterilizing substances and sterilized by the steam or the steam and other sterilizing substances is present in the at least a portion of the sealed interior space.

9. The method of claim 8, wherein the atmosphere is steam saturated.

10. The method of claim 9, wherein the atmosphere is steam saturated under conditions of 20° C. and a pressure of 101.325 kPa.

11. The method of claim 8, wherein the atmosphere is a steam-sterilized or steam and EtO-sterilized gas atmosphere.

12. The method of claim 1, wherein:

the second sub-section comprising a window of a gas or steam permeable material, wherein volumes of the first and second interior space areas are connected to one another; and the packaging further comprises a structure positioned in a transition area between the first and second interior space areas to separate the first interior space area from the second interior space area in a gas-tight manner.

13. The method of claim 12, wherein the packaging is formed as a container with a cover, the container having a perimeter edge against which the cover seals the container, wherein the container has at least one first depression which delimits the first interior space area and at least one second depression which delimits the second interior space area, and wherein the window is formed in an area of the cover that covers the second interior space area.

14. The method of claim 13, wherein the structure defines a surface configured for sealing to the cover and is co-planar in relation to the perimeter edge of the container.

15. The method of claim 13, wherein the cover is comprised of a foil material and the window is comprised of a non-woven fabric of high-density polyethylene or an autoclave paper.

16. The method of claim 12, wherein the packaging further comprises an additional structure adjacent to the structure that is raised relative to the structure and that raises the cover above the perimeter edge of the container when fastened thereto and above the structure so that a passage between the first sub-section and the second sub-section remains free between the structure and the cover for gas exchange.

17. The method of claim 16, wherein the additional structure is configured on an inside of the packaging to prevent the packaging from collapsing onto itself.

18. The method of claim 12, wherein the packaging is comprised of a plastic.

19. The method of claim 18, wherein the packaging is comprised of polypropylene (PP), polyethylene terephthalate (PET) or a combination thereof.

\* \* \* \* \*